United States Patent [19]

Endo et al.

[11] Patent Number: 5,296,373
[45] Date of Patent: Mar. 22, 1994

[54] PROCESS FOR PRODUCING R(−)-MANDELIC ACID OR A DERIVATIVE THEREOF FROM A MANDELONITRILE USING RHODOCOCCUS

[75] Inventors: Takakazu Endo; Koji Tamura, both of Kanagawa, Japan

[73] Assignee: Nitto Chemical Industry Co., Ltd., Tokyo, Japan

[21] Appl. No.: 904,335

[22] Filed: Jun. 25, 1992

[30] Foreign Application Priority Data

Jun. 26, 1991 [JP] Japan .................. 3-180475

[51] Int. Cl.$^5$ ............. C12P 41/00; C12P 7/42
[52] U.S. Cl. ................. 435/280; 435/146; 435/822
[58] Field of Search ............ 435/280, 146, 822

[56] References Cited

U.S. PATENT DOCUMENTS 4,859,784  8/1989  Effenberger et al. ........... 549/491
5,008,192  4/1991  Neidermeyer et al. ........... 435/128

FOREIGN PATENT DOCUMENTS 0098707  1/1984  European Pat. Off. .
0348901  1/1990  European Pat. Off. .
0449648  10/1991 European Pat. Off. .
57-198096 12/1982 Japan .
58-177933 10/1983 Japan .

OTHER PUBLICATIONS

Kakeya H et al., Agric Biol. Chem. 55:1877-81 (1991).
ATCC Catalog of Bacteria & Bacteriophages pp. 184-188 (1989).
Mori et al., "Synthesis of Optically Active Alkynyl . . . Acetates", Tetrahedron, vol. 36, pp. 91-96 (1980).
Evans et al., "Asymmetric Oxygenation of Chiral . . . Acid Synthons", J. Am. Chem. Soc., vol. 107, pp. 4346-4348 (1985).
Yamazaki et al., "Enzymatic Synthesis of Optically . . . and Use", Agric. Biol. Chem., vol. 50, pp. 2621-2631 (1986).

Primary Examiner—Douglas W. Robinson
Assistant Examiner—S. Saucier
Attorney, Agent, or Firm—Sughrue, Mion, Zinn, Macpeak & Seas

[57] ABSTRACT

A process for treating R,S-mandelonitrile or a derivative thereof or a mixture of benzaldehyde or a derivative thereof, and; hydrogen cyanide, with a microorganism belonging to the genus Rhodococcus sp. HT29-7 (FERM BP-3857) in an almost neutral or basic aqueous medium to thereby directly produce a predominant amount of R(−)-mandelic acid or a derivative thereof, whereby the racemic R,S-mandelonitrile or a derivative thereof or benzaldehyde or a derivative thereof and hydrogen cyanide can be directly converted into R(−)-mandelic acid or a derivative thereof at a ratio of about 80 to 100% and at an optical purity of almost 100%$_{ee}$ without performing any optical resolution.

5 Claims, No Drawings

PROCESS FOR PRODUCING R(—)-MANDELIC ACID OR A DERIVATIVE THEREOF FROM A MANDELONITRILE USING RHODOCOCCUS

FIELD OF THE INVENTION

This invention relates to R(—)-mandelic acid or a derivative thereof. More particularly, it relates to a process for producing R(—)-mandelic acid represented by the following general formula (III) or a derivative thereof. The process is carried out by using a microorganism belonging to the genus Rhodococcus which is capable of effecting nitrile asymmetric hydrolysis of R,S-mandelonitrile represented by the following general formula (I) or a derivative thereof. Compounds having a mandelic acid skeleton are highly valuable from an industrial viewpoint as starting materials for producing cephem-series antibiotics and a number of medicines and agricultural chemicals.

BACKGROUND OF THE INVENTION

Known methods for producing R(—)-mandelic acid or derivatives thereof include: racemic resolution of chemically synthesized R,S-mandelic acid (racemic modification) by (1) fractional crystallization as described in JP-A-58-177933 (the term "JP-A" as used herein means an "unexamined published Japanese patent application"); (2) chromatography as described in European Patent Publication No. 0 098 707A; and (3) conversion of the racemic modification into racemic esters followed by racemic resolution thereof by enzymatic asymmetric hydrolysis as described in K. Mori et al., *Tetrahedron*, 36, 91–96 (1980); and (4) chemical asymmetric synthesis with the use of a chiral reagent as described in D. A. Evans et al., *J. Am. Chem. Soc.*, 107, 4346–4348 (1985). Biological methods therefor include the asymmetric hydrolysis of the abovementioned esters formed by process (3) above and (5) microbiological asymmetric reduction of benzoylformic acid as described in JP-A-57-198096; (6) hydrolysis of R(—)-mandelonitrile or substituted derivatives thereof which are asymmetrically synthesized with the use of D-oxynitrilase as described in U.S. Pat. Nos. 4,859,784 and 5,008,192; and (7) asymmetric hydrolysis of mandelonitrile, mandelamide or substituted derivatives thereof with the use of microorganisms belonging to the genus Alcaligenes, Pseudomonas, Rhodopseudomonas, Corynebacterium, Acinetobacter, Bacillus, Mycobacterium, Rhodococcus or Candida as described in European Patent Publication No. 0 348 901A.

However, each of the racemic resolution methods (1) to (3) requires a complicated process and a decrease in the yield occurs in each step. In method (4), using a chiral reagent as a catalyst, an expensive chiral reagent is required and a product of high optical purity is almost impossible to obtain.

The above-mentioned biological methods also have some disadvantages. Namely, in method (5) it is difficult to synthesize the substrate for the asymmetric reduction of benzoylformic acid. It is further difficult to maintain the NADH-regeneration system. The D-oxynitrilase method (6) is merely a basic finding that an optically active substance is obtained. The asymmetric hydrolysis method (7) requires a post treatment of another optically active substance remaining after the completion of the hydrolysis. In addition, the above-mentioned European Patent Publication No. 0 348 901A contains no particular example of the production of a R(—)-mandelic acid derivative from a substituted derivative of mandelonitrile. Therefore, it is unknown whether an R(—)-mandelic acid derivative of a high optical purity can be efficiently obtained or not.

As described above, these known methods suffer from various problems. Thus, none of these known methods is an industrially advantageous method for producing R(—)-mandelic acid or derivatives thereof.

The present inventors conducted extensive investigations to establish a method for advantageously producing R(—)-mandelic acid on an industrial scale. As a result, the present inventors discovered that R,S,-mandelonitrile could be easily racemized through dissociation equilibrium into benzaldehyde and hydrogen cyanide in an almost neutral or basic aqueous medium, and that R,S-mandelonitrile or benzaldehyde and hydrogen cyanide could be directly converted into R(—)-mandelic acid in conjunction with this racemization system together with a microorganism capable of asymmetric hydrolysis of mandelonitrile. Based on these findings, they disclosed a process for producing R(—)-mandelic acid by using a microorganism belonging to the genus Pseudomonas, Alcaligenes, Acinetobacter or Caseobacter as described in European Patent Publication No. 0 449 648A and another process for producing R(—)-mandelic acid with the use of a microorganism belonging to the genus Nocardia, Bacillus, Brevibacterium or Aureobacterium as described in European Patent Publication No. 0 449 648A. Subsequently, they further applied the above-mentioned findings to substituted mandelonitrile derivatives and, as a result, proposed a process for producing R(—)-mandelic acid derivatives with the use of a microorganism belonging to the genus Aureobacterium, Pseudomonas, Caseobacter, Alcaligenes, Acinetobacter, Brevibacteriumn or Nocardia as described in European Patent Publication No. 0 449 648A.

However, the R-stereoselectivities of the hydrogenases produced by these bacteria are not always satisfactory and thus further evaluation has been required for the steroeselectivities.

SUMMARY OF THE INVENTION

The present inventors have further attempted to find a microorganism possessing an excellent capability of asymmetrically hydrolyzing mandelonitrile or derivatives thereof. As a result, they have successfully discovered that an extremely high R-stereoselectivity can be achieved by using a microorganism belonging to the genus Rhodococcus, thus completing the present invention.

Accordingly, the present invention provides a process for producing a predominant amount of R(—)-mandelic acid represented by the following general formula (III) or a derivative thereof from R,S-mandelonitrile represented by the following general formula (I) or a derivative thereof or from benzaldehyde represented by the following general formula (II) or a derivative thereof and hydrogen cyanide, by treating a R,S-mandelonitrile of general formula (I) or a derivative thereof or a mixture of benzaldehyde of general formula (II) or a derivative thereof and hydrogen cyanide, using a microorganism, which may be treated, belonging to the genus Rhodococcus and capable of stereoselectively hydrolyzing the nitrile group in a R,S-mandelonitrile represented by the general formula (I) or a derivative thereof in a substantially neutral or basic aqueous medium:

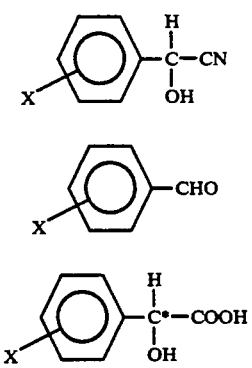

(I)

(II)

(III)

wherein X, which is located at the o-, m- or p-position, is selected from the group consisting of a hydrogen atom, a halogen atom, a hydroxy group, an alkyl group having 1 to 3 carbon atoms, an alkoxy group having 1 to 3 carbon atoms, a thioalkyl group having 1 to 3 carbon atoms, an amino group, a nitro group, a mercapto group, a phenyl group and a phenoxy group.

DETAILED DESCRIPTION OF THE INVENTION

As described above, the present invention has been completed by further applying the above-mentioned findings of the present inventors, i.e., R,S,-mandelonitrile capable of being easily racemized through a dissociation equilibrium into benzaldehyde and hydrogen cyanide in a substantially neutral or basic aqueous medium, and R,S-mandelonitrile or benzaldehyde and hydrogen cyanide capable of being directly converted into R(−)-mandelic acid in conjunction with the above described racemization system together with a microorganism capable of R-stereoselective hydrolysis of mandelonitrile to the R,S-mandelonitrile derivatives represented by the general formula (I) and by using a microorganism having an extremely high R-stereoselectivity as the above-mentioned microorganism.

The expression "predominant amount" as used herein means that the starting R,S-mandelonitrile represented by the general formula (I) or a derivative thereof or a mixture of benzaldehyde represented by the general formula (II) or a derivative thereof and hydrogen cyanide, can be directly converted into the target R(−)-mandelic acid represented by the general formula (III) or a derivative thereof at a ratio of "50% or above".

The microorganism to be used in the present invention is a microorganism belonging to the genus Rhodococcus. Rhodococcus sp. HT29-7 (FERM BP-3857) may be cited as a particular example thereof. This strain was isolated from soil by the present inventors for the first time and deposited with Fermentation Research Institute, Agency of Industrial Science and Technology, 1-3, Higashi 1-chome, Tsukuba-shi, Ibaraki, Japan under the above-mentioned accession number. The bacteriological properties of this strain are as follows.

| Strain HT29-7: | |
|---|---|
| Morphotype: | polymorphobacillus |
| Gram-staining: | + |
| Sporulation: | − |
| Motility: | − |

-continued

| Strain HT29-7: | |
|---|---|
| Colony color: | pink to orange |
| Rod-coccus cycle: | + |
| Elongation of cell around colonies: | yes |
| Formation of mycelia: | no |
| Oxidase: | − |
| Catalase: | + |
| Oxygen requirement: | aerobic |
| Diamino acid in cell wall: | meso-diaminopimelic acid |
| Glycolyl test: | + (glycolyl type) |
| Sugar composition of cell wall: | |
| arabinose: | + |
| galactose: | + |
| Quinone system: | MK-9(H$_2$) |

Based on these bacteriological properties, this strain HT29-7 was identified as a bacterium belonging to the genus Rhodococcus according to *Bergey's Manual of Systematic Bacteriology*, 1986.

Examples of the compound represented by the above-mentioned general formula (I) include mandelonitrile, chloromandelonitrile, bromomandelonitrile, fluoromandelonitrile, hydroxymandelonitrile, methylmandelonitrile, ethylmandelonitrile, isopropylmandelonitrile, methoxy-mandelonitrile, methylthiomandelonitrile, mercaptomandelonitrile, aminomandelonitrile, nitromandelonitrile, phenylmandelonitrile and phenoxymandelonitrile each having a substituent at the o-, m- or p-position.

The compound represented by the general formula (II) includes a benzaldehyde corresponding to the above-mentioned compounds as well as derivatives thereof.

The microorganism to be used in the present invention may be incubated in a medium commonly employed in the art containing 0.5 to 20% carbon sources (for example, glycerol, glucose, saccharose) and 0.5 to 10% nitrogen sources (for example, casamino acids, meat extract, yeast extract), which can be utilized by the microorganism, and mineral salts (for example, magnesium chloride, calcium chloride, manganese sulfate, iron chloride, zinc sulfate) which are essential for the growth of the microorganism.

It is preferable to add nitriles (for example, cinnamyl nitrile, benzyl cyanide, isobutyronitrile, β-phenyl-propionitrile, benzonitrile, 2-cyanopyridine, 3-cyanopyridine, 4-cyanopyridine, 1-cyclohexenyl acetonitrile, ε-caprolactam, ε-butyronitrile, o-aminobenzonitirle) or amides (for example, isobutylamide, phenylacetamide, 4-pyridylcarboxylic acid amide) to the medium at such a concentration so as not to considerably inhibit the growth of the microorganism during the early or medium stage of the incubation, since the enzymatic activity can be further elevated thereby.

The incubation may be carried out at a pH value of the medium of from 4 to 10 (preferably from 6 to 9) and at a temperature of from 5° to 50° C. (preferably from 25° to 40° C.) under aerobic conditions for approximately 1 to 14 days (preferably 3 to 7 days).

The hydrolysis may be carried out in the following manner. Cells or treated cells (for example, ground cells, crude or purified enzymes, immobilized cells, immobilized enzymes) of the microorganism, which has been incubated by the above-mentioned method, are suspended in an aqueous medium such as water or a buffer solution. Then, the obtained suspension is mixed with the R,S-mandelonitrile represented by the general formula (I) or a derivative thereof or a mixture of benzaldehyde represented by the general formula (II) or a derivative thereof and hydrogen cyanide. As described above, it is required in the present invention to maintain the reaction system at a substantially neutral or basic state throughout the reaction in order to racemize the mandelonitrile or a derivative thereof. Therefore, the pH value of the reaction system is adjusted to from 6 to 11 (preferably from 7 to 9).

In the reaction mixture, the content of the mandelonitrile or a derivative thereof may range from 0.1 to 10% by weight (preferably from 0.2 to 5.0% by weight), the content of the benzaldehyde or a derivative thereof may range from 0.1 to 10% by weight (preferably from 0.2 to 5.0% by weight) and the content of the hydrogen cyanide may range from 0.1 to 2.0% by weight (preferably from 0.1 to 0.5% by weight). Based on the substrates, the microorganism may be used at a ratio of from 0.01 to 5.0% by dry weight (preferably from 0.1 to 2% by dry weight). The reaction temperature may range from 0° to 50° C., preferably from 10° to 30° C. The reaction may be performed for 0.1 to 100 hours (preferably for 5 to 30 hours).

The R(—)-mandelic acid thus obtained or a derivative thereof are then treated as follows. The cells are removed from the reaction mixture by a known procedure such as centrifugation and then granular components, proteins and polysaccharide components are further removed, if required, by, for example, ultrafiltration. Then, the residue is optionally treated with activated carbon and concentrated under reduced pressure, or extracted with an organic solvent under acidic conditions. After repeated recrystallization from, for example, benzene, the target product is obtained as crystals of a high purity.

According to the present invention, R,S-mandelonitrile of racemic modification or a derivative thereof or benzaldehyde or a derivative thereof and hydrogen cyanide can be directly converted into R(—)-mandelic acid or a derivative thereof at a ratio of about 80 to 100% and at an optical purity of almost 100%$ee$ without performing any optical resolution. Thus, the process for producing R(—)-mandelic acid or a derivative thereof of the present invention is highly superior to known methods in terms of operation and cost.

The following Examples are given to further illustrate the present invention in greater detail, and not for the purpose of limiting thereto.

EXAMPLE 1

(1) Incubation of Microorganism and Preparation of Cell Suspension

Rhodococcus sp. HT29-7 was incubated in the following medium A at 30° C. for 72 hours and the cells thus obtained were further incubated in the medium B at 30° C. for 96 hours.

| i) Media (Medium A) | |
| --- | --- |
| Glycerol | 20 g |
| Yeast extract | 6 g |
| Monopotassium phosphate | 6.8 g |
| Dipotassium phosphate | 7.1 g |
| Sodium sulfate | 2.8 g |
| Magnesium chloride | 0.4 g |
| Calcium chloride | 0.04 g |
| Manganese sulfate | 0.03 g |
| Iron chloride | 0.006 g |
| Zinc sulfate | 0.003 g |
| Distilled water | 1000 ml |

| -continued | |
| --- | --- |
| pH | 7.5 |

Medium B 0.02% (weight/volume) of 1-cyclohexenyl acetonitrile was further added to the above Medium A.

The cells were separated from the obtained incubation broth and washed with a 50 mM phosphate buffer solution (pH 8.0). Next, the cells were suspended in 100 ml of this same phosphate buffer solution to form a cell suspension ($OD_{630}=28.3$, 1.13% by dry weight).

(2) Asymmetric hydrolysis of mandelonitrile

To the cell suspension obtained above, mandelonitrile was continuously added with the use of a micro-test tube pump at a flow rate of 5.35 mmol/hr and the reaction was carried out at 30° C. After adding mandelonitrile for one hour, R(—)-mandelic acid and ammonia were formed substantially quantitatively based on the consumed mandelonitrile.

The reaction was carried out for 4 hours total under the above-mentioned conditions. When analyzed by liquid chromatography with the use of an ODS column, 3.4% (weight/volume) of ammonium R(—)-mandelate was accumulated from 2.8 g of the starting mandelonitrile 4 hours after the initiation of the reaction (conversion yield: 94.1%). After the completion of the reaction, the cells were removed from the reaction mixture, the thus obtained reaction mixture was treated with an acid so as to give a pH value of 2. The aqueous phase was then extracted with ethyl acetate, thereby forming mandelic acid. The aqueous solution of mandelic acid thus obtained was dried over sodium sulfate anhydride. The organic solvent was then distilled off, thereby forming crude crystals. The crystals were further recrystallized from a mixed solvent of benzene/ethyl acetate (7:1 by volume) to thereby form 2.8 g of crystals in the form of a white powder. These crystals and standard R(—)-mandelic acid were each formulated into an aqueous solution of 1.0% (weight/volume) using distilled water. Next, the specific rotation of each aqueous solution was measured with a rotational meter and the optical purity thereof was determined by high performance liquid chromatography using an optical resolution column (MCI GEL CRS10W). The analytical data thus obtained is shown in Table 1 below.

TABLE 1

| Sample | Specific Rotation $[\alpha]_D^{20}$ | Optical Purity (%$ee$) |
| --- | --- | --- |
| Example 1 | −150 | 100 |
| Standard | −153 | 100 |

EXAMPLE 2

(1) Incubation of Microorganism and Preparation of Cell Suspension

Rhodococcus sp. HT29-7 was incubated under the same conditions and a cell suspension was prepared ($OD_{630}=12$, 0.48% by dry weight) with 50 mM phosphate buffer solution at pH 8.0, as those described in Example 1.

(2) Asymmetric Hydrolysis of Various Substrates

Various mandelonitrile derivatives or hydrogen cyanide and benzaldehyde derivatives as listed in Table 2 were added to the 10 ml each of above-mentioned cell suspension each at a concentration specified in Table 2 and then the reaction was carried out at 30° C. for 17 hours while shaking.

After the completion of the reaction, the cells were removed by centrifugation from the reaction mixture and the reaction yield and the optical purity of the obtained product were determined by high performance liquid chromatography with the use of both ODS and optical resolution column (MCI GEL CRS10W) by the same method as the one described in Example 1. The results are shown in Table 2 below.

TABLE 2

| Substrate | Amount (mM) | R(—)-Mandelic Acid/Derivative | | | |
|---|---|---|---|---|---|
| | | X | Formed (mM) | Yield (%) | Optical Purity (%ee) |
| Benzaldehyde | 10 | H— | 9.8 | 98 | 100 |
| Hydrogen Cyanide | 11 | | | | |
| 2-Chloromandelonitrile | 7 | 2Cl— | 6.8 | 97 | 100 |
| 3-Chloromandelonitrile | 6 | 3Cl— | 4.6 | 77 | 100 |
| 4-Chloromandelonitrile | 7 | 4Cl— | 4.5 | 64 | 100 |
| 4-Hydroxybenzaldehyde | 4 | 4HO— | 3.5 | 88 | 100 |
| Hydrogen Cyanide | 4 | | | | |
| 4-Methylbenzaldehyde | 4 | 4CH$_3$— | 3.7 | 93 | 100 |
| Hydrogen Cyanide | 5 | | | | |
| 4-Methoxybenzaldehyde | 3 | 4CH$_3$O— | 2.5 | 83 | 100 |
| Prussic acid | 3 | | | | |

While the invention has been described in detail and with reference to specific embodiments thereof, it will be apparent to one skilled in the art that various changes and modifications can be made therein without departing from the spirit and scope thereof.

What is claimed is:

1. A process for producing a R(—)-mandelic acid represented by the following general formula (III) directly from a R,S-mandelonitrile represented by the following general formula (I) or from a benzaldehyde represented by the following general formula (II) and hydrogen cyanide by treating (A) the R,S-mandelonitrile of general formula (I) or (B) a mixture of the benzaldehyde of general formula (II) and hydrogen cyanide, with Rhodococcus sp. HT29-7 (FERM BP-3857) which stereoselectively hydrolyzes the nitrile group of the R,S-mandelonitrile represented by the general formula (I) in a substantially neutral or basic aqueous medium and recovering the produced R(—)-mandelic acid of general formula (III):

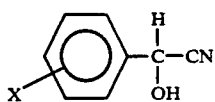 (I)

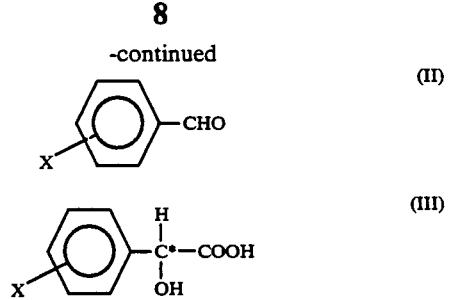

wherein X, is selected from the group consisting of a hydrogen atom, a halogen atom, a hydroxy group, an alkyl group having 1 to 3 carbon atoms, an alkoxy group having 1 to 3 carbon atoms, a thioalkyl group having 1 to 3 carbon atoms, an amino group, a nitro group, a mercapto group, a phenyl group and a phenoxy group.

2. The process for producing a R(—)-mandelic acid as claimed in claim 1, wherein R(—)mandelic acid is produced in a yield of 50% or above.

3. The process for producing a R(—)-mandelic acid as claimed in claim 1, wherein R(—)-mandelic acid or a derivative thereof is formed in a yield of 80 to 100%.

4. The process for producing a R(—)-mandelic acid as claimed in claim 1, wherein the R,S-mandelonitrile is selected from the group consisting of mandelonitrile, chloromandelonitrile, bromomandelonitrile, fluoromandelonitrile, hydroxymandelonitrile, methylmandelonitrile, ethylmandelonitrile, isopropylmandelonitrile, methoxymandelonitrile, methylthiomandelonitrile, mercaptomandelonitrile, aminomandelonitrile, nitromandelonitrile, phenylmandelonitrile and phenoxymandelonitrile.

5. The process for producing a R(—)-mandelic acid as claimed in claim 1, wherein the pH value of said aqueous medium is from 6 to 11.

* * * * *